United States Patent [19]

Gross et al.

[11] Patent Number: 4,886,820

[45] Date of Patent: Dec. 12, 1989

[54] DIHYDROPYRIDINE COMBINATION PRODUCT COMPRISING A DIHYDROPYRIDINE COMPOUND AND A CARDIOACTIVE NITRATE

[75] Inventors: Rainer Gross, Wuppertal; Matthias Schramm, Cologne, both of Fed. Rep. of Germany

[73] Assignee: Bayer Aktiengesellschaft, Leverkusen, Fed. Rep. of Germany

[21] Appl. No.: 274,182

[22] Filed: Nov. 3, 1988

Related U.S. Application Data

[63] Continuation-in-part of Ser. No. 98,353, Sep. 18, 1987, abandoned, which is a continuation-in-part of Ser. No. 875,139, Jun. 17, 1986, abandoned.

[30] Foreign Application Priority Data

Jul. 2, 1985 [DE] Fed. Rep. of Germany ....... 3523540

[51] Int. Cl.$^4$ ..................... A61K 31/34; A61K 31/44
[52] U.S. Cl. .................................. 514/356; 514/470; 514/338
[58] Field of Search ..................... 514/356, 470, 338

[56] References Cited

FOREIGN PATENT DOCUMENTS 1173862 12/1969 United Kingdom .
2084017 4/1982 United Kingdom .

OTHER PUBLICATIONS

Abshagen et al; Eur. J. Clin. Pharmacol (1981) 20: 269–275.
Dialog 5888327, Embase No. 85133837 G. P. Dube et al, "Effects of a novel calcium . . . and nimodipine" (1985).

*Primary Examiner*—Allen J. Robinson
*Attorney, Agent, or Firm*—Sprung Horn Kramer & Woods

[57] ABSTRACT

A solid medicament formulation which can be administered orally, comprising 1 to 40 mg of a dihydropyridine of the formula

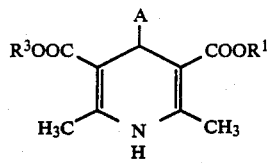

in which
  $R^1$ and $R^3$ are always different from one another and represent alkyl which has 1 to 12 carbon atoms and which is optionally substituted once or several times by fluorine or chlorine or which is optionally interrupted by an oxygen atom in the chain, and
  A represents the radical

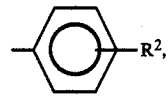

$R^2$ representing one or two substituents from the group consisting of nitro, chlorine and trifluoromethyl, or represents

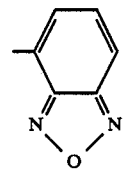

and 0.1 to 100 mg of a cardioactive nitrate. The composition is cardio-active and the patient's tendency toward nitrate tolerance is reduced.

5 Claims, No Drawings

DIHYDROPYRIDINE COMBINATION PRODUCT COMPRISING A DIHYDROPYRIDINE COMPOUND AND A CARDIOACTIVE NITRATE

This is a continuation-in-part of Application Ser. No. 098,353 filed Sept. 18, 1987, now abandoned, which is a continuation-in-part of Ser. No. 875,139, filed June 17, 1986, now abandoned.

The present invention relates to a solid combination product containing a dihydropyridine and a nitrate, which can be used for the chronic treatment of heart diseases, especially of diseases of the coronaries and of the myocardium in humans and other animals.

The dihydropyridines which are used as known (British Patent No. 1,358,951). Their use as cardiovascular agents is also known.

The nitrates which are used (in particular isosorbide 5-mononitrate (IS-5-MN) and isosorbide dinitrate (ISDN)) are known. They also have vasodilator actions, there being a preferential action on the veins on treatment of heart diseases. On chronic treatment of heart diseases with nitro products of this type there is frequently an undesired development of tolerance, which makes an increase in the dosage necessary or no longer shows an adequate therapeutic action.

The invention relates to solid medicament formulations which can be administered orally for use for the chronic control of heart diseases, in particular diseases of the coronaries and of the myocardium, containing 1 to 40 mg of a dihydropyridine of the general formula I

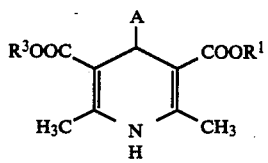

in which

R$^1$ and R$^3$ are always different from one another and represent alkyl which has 1 to 12 carbon atoms and which is optionally substituted once or several times by fluorine or chlorine or which is optionally interrupted by an oxygen atom in the chain, and A represents the radical

R$^2$ representing one or two substituents from the group comprising nitro, chlorine and trifluoromethyl, or represents

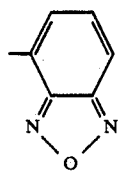

and 0.1 to 100 mg of nitrates and, where appropriate, customary auxiliaries and vehicles.

Particular interest attaches to those combination products which contain 5 to 30 mg of the dihydropyridine and 10 to 30 mg of isosorbide 5-mononitrate or 5 to 50 mg of isosorbide dinitrate. Such combination will be effective taken two or three times daily by an adult human weighing 150 pounds.

Particularly preferred dihydropyridines are nisoldipine and nitrendipine.

Surprisingly, when the combination according to the invention is used there is prevention of the development of tolerance to the nitrate component. This can be demonstrated in experiments on isolated tissues. Thus, for example, the development of tolerance to nitrates can be detected by determination of their action on the serotonin-induced contraction of pulmonary veins (U. Borchard et al., Med. Klin. Special Issue 1 (1985), 21-23).

If, in these experiments, the effect of the substance immediately after administration of the substance is set equal to 100%, then the decrease in this effect with time is a measure of the development of tolerance. The following figures emerge after five hours (or after 2 in the ISDN experiments):

|  | Concentration (g/ml) | | | Loss of effect |
| --- | --- | --- | --- | --- |
| ISMN | ISDN | Nitrendipine | Nisoldipine | after 5 (2) h |
| $10^{-4}$ | 0 | 0 | 0 | 42 |
| $3 \times 10^{-4}$ | 0 | 0 | 0 | 48 |
| 0 | $3 \times 10^{-6}$ | 0 | 0 | 100 |
| 0 | $10^{-5}$ | 0 | 0 | 100 |
| 0 | 0 | $10^{-6}$ | 0 | 2 |
| 0 | 0 | $3 \times 10^{-6}$ | 0 | 0 |
| 0 | 0 | 0 | $10^{-7}$ | 0 |
| 0 | 0 | 0 | $3 \times 10^{-7}$ | 0 |
| $10^{-4}$ | 0 | $10^{-6}$ | 0 | 9 |
| 0 | $3 \times 10^{-6}$ | $10^{-6}$ | 0 | 4 |
| $10^{-4}$ | 0 | 0 | $10^{-7}$ | 8 |
| 0 | $3 \times 10^{-6}$ | 0 | $10^{-7}$ | 3 |

This unexpected finding is a crucial advantage, especially in the chronic treatment, which is necessary, of the heart diseases mentioned.

Furthermore, the present invention makes it possible for those skilled in the art to achieve the same therapeutic effect with considerably reduced dosage of the active compounds. This means that adverse side effects are reduced. This is likewise a great advantage on chronic treatment.

The example which follows illustrates a specific embodiment of the combination products according to the invention, without having a restrictive action.

PREPARATION EXAMPLE

Example 1

10 g of nisoldipine (microfine) are mixed with 80 g of a trituration of IS-5-MN in lactose (25% strength), 41.4 g of corn starch, 15 g of lactose and 20 g of Avicel, and then granulated with a solution of 0.8 g of sodium lauryl sulphate in 12 g of polyvinylpyrrolidone (PVP 25). The granules are dried, screened and mixed with 0.8 g of magnesium stearate. Tablets with a mean tablet weight of 180 mg are compressed from this mixture, or the mixture is dispensed into hard gelatin capsules with a capsule capacity of 180 mg.

It will be understood that the specification and examples are illustrative but not limitative of the present invention and that other embodiments within the spirit and scope of the invention will suggest themselves to those skilled in the art.

What is claimed is:

1. A solid medicament formulation for treatment of diseases of the coronaries and of the myocardium and which can be administered orally, comprising a synergistically effective mixture of a dihydropyridine selected from the group consisting of nisoldipine and nitrendipine and a cardioactive nitrate selected from the group consisting of isosorbide-5-mononitrate and isosorbide-dinitrate, wherein there is one part of the dihydropyridine per 1 to 1000 parts of the nitrate.

2. A method of treating a patient having a disorder of the coronaries, which method comprises orally administering to such patient an amount effective therefor of a medicament formulation according to claim 1.

3. A method of treating a patient having a disorder of the myocardium, which method comprises orally administering to such patient an amount effective therefor of a medicament formulation according to claim 1.

4. A medicament formulation according to claim 1, wherein there is 1 part of the dihydropyridine per 1 to 100 parts of the nitrate.

5. A medicament formulation according to claim 1, wherein there is 1 part of the dihydropyridine per 1 to 30 parts of the nitrate.

* * * * *